(12) United States Patent
Kang et al.

(10) Patent No.: US 11,484,511 B2
(45) Date of Patent: Nov. 1, 2022

(54) PHARMACEUTICAL COMPOSITION COMPRISING THA AS EFFECTIVE INGREDIENT FOR TREATMENT OF PROSTATE CANCER

(71) Applicant: KOREA UNITED PHARM. INC., Sejong (KR)

(72) Inventors: Keon Wook Kang, Seoul (KR); Sung Baek Jeong, Seoul (KR)

(73) Assignee: KOREA UNITED PHARM, INC., Sejong (KR)

( * ) Notice: Subject to any disclaimer, the term of this patent is extended or adjusted under 35 U.S.C. 154(b) by 235 days.

(21) Appl. No.: 15/733,370

(22) PCT Filed: Dec. 26, 2018

(86) PCT No.: PCT/KR2018/016625
§ 371 (c)(1),
(2) Date: Jul. 10, 2020

(87) PCT Pub. No.: WO2019/139283
PCT Pub. Date: Jul. 18, 2019

(65) Prior Publication Data
US 2021/0093583 A1 Apr. 1, 2021

(30) Foreign Application Priority Data
Jan. 10, 2018 (KR) .................. 10-2018-0003229

(51) Int. Cl.
*A61K 31/12* (2006.01)
*A61P 35/00* (2006.01)
*A61K 36/9066* (2006.01)

(52) U.S. Cl.
CPC .......... *A61K 31/12* (2013.01); *A61K 36/9066* (2013.01); *A61P 35/00* (2018.01); *A61K 2236/331* (2013.01)

(58) Field of Classification Search
CPC ...... A61K 31/12; A61K 36/9066; A61P 35/00
See application file for complete search history.

(56) References Cited

FOREIGN PATENT DOCUMENTS

| | | |
|---|---|---|
| JP | 2001-199881 A | 7/2001 |
| JP | 2010-209055 A | 9/2010 |
| KR | 10-1819509 B | 1/2018 |

OTHER PUBLICATIONS

Japanese Office Action dated Jul. 2, 2021, for corresponding JP Patent Application No. 2020-537145, 9 pages.
Nakamura et al., "Cancer chemopreventive effects of constituents of Caesalpinia ferrea and related compounds", Cancer Letters, 2002, vol. 177, pp. 119-124.
Cho et al., "Geranyl derivative of phloracetophenone induces cancer cell specific apoptosis through bax-mediated mitochondrial pathway in MCF-7 human breast cancer cells", Biological and Pharmaceutical Bulletin, 2012, vol. 35(1), pp. 98-104.
Cho, "Apoptosis-inducingactivity of syntheticpolyphenolcompound, 3-geranyl-2,4,6-trihydraxyacetophenone, in MCF-7 and adriamycin-resistant MCF-7 breast cancer cells", Yeungnam University, Master's thesis, 2010.
Ferreira et al., "The 2', 4', 6'-trihydroxyacetophenone isolated from Myrcia multiflora has antiobesity and mixed hypolipidemic effects with the reduction of lipid intestinal absorption", Planta medica, 2011, vol. 77(14), pp. 1569-1574.
Piyachaturawat et al., "Choleretic activity of phloracetophenone in rats: structure-function studies using acetophenone analogues", European journal of pharmacology, 2000, vol. 387(2), pp. 221-227.

*Primary Examiner* — Barbara P Badio
(74) *Attorney, Agent, or Firm* — Vorys, Sater, Seymour and Pease LLP; Mih Suhn Koh

(57) ABSTRACT

The present invention relates to a composition comprising 2,4,6-trihydroxyacetophenone (THA) as an effective ingredient for prevention or treatment of prostate cancer. THA in the present invention is a main ingredient of *Curcuma comosa*. The composition of the present invention effectively inhibits the growth of prostate cancer by regulating in particular the activity of polo-like kinase 1 (PLK1) and thus is expected to find useful applications in use in the prevention, alleviation, and treatment of prostate cancer in future.

1 Claim, 10 Drawing Sheets

PHARMACEUTICAL COMPOSITION COMPRISING THA AS EFFECTIVE INGREDIENT FOR TREATMENT OF PROSTATE CANCER

CROSS-REFERENCE TO RELATED APPLICATIONS

This application is a 371 of PCT/KR2018/016625, filed Dec. 26, 2018, which claims the benefit of priority from Korean Patent Application No. 10-2018-0003229, filed Jan. 10, 2018, the contents of each of which are incorporated herein by reference in its entirety.

TECHNICAL FIELD

The present invention relates to a composition comprising 2,4,6-trihydroxyacetophenone (THA) as an effective ingredient for prevention or treatment of prostate cancer.

BACKGROUND ART

*Curcuma comosa* is a plant of the genus *Curcuma* which is widely used as a raw material of health functional food in Southeast Asia such as Thailand and Vietnam, and is known to be particularly effective for vaginal atrophy or vasodilation in postmenopausal women, and the like due to its action similar to that of the female hormone estrogen. As an effective ingredient of *Curcuma comosa*, the diarylheptanoid series is known, and it has been revealed that the compound affects the processes of hepatocyte protection (liver protection), melanin production inhibition (whitening), or promotion of osteoblast differentiation (improvement of osteoporosis). Further, it is known that an extract of *Curcuma comosa* has an effect of reducing blood cholesterol, which is known as an action of 2,4,6-trihydroxyacetophenone (THA, Phloracetophenone), which is another effective ingredient of *Curcuma comosa*, but the anticancer activity of the compound is not yet known.

Meanwhile, prostate cancer refers to cancer that has developed in the prostate, and is a representative male cancer disease with the highest prevalence and second highest mortality among all male cancers in the United States and Europe. It has been reported that the incidence is lower in Korea compared to Western countries, but malignancy is high, and the incidence of prostate cancer tends to be rapidly increasing such that the rate of increase is the highest among male cancers due to the universal adoption of Western-style dietary habits, an increase in the elderly population, and the development of diagnostic technology. Although the cause of prostate cancer has not been clarified yet, it is known that not only age, race, family history, genetic predisposition, but also hormones, dietary habits, and chemicals such as herbicides serve as important factors in the onset thereof.

The treatment of prostate cancer varies depending on the stage of the disease, but early prostate cancer is preceded by a fundamental treatment which removes cancer cells by surgery and radiation therapy, and when the cancer cells have spread from the prostate gland and metastasized to the surrounding regions, the patient receives hormone treatment. Male hormones are known to promote the growth of prostate cancer, so that it is possible to delay or prevent the progression of prostate cancer by inhibiting male hormones. However, when a patient receives the hormone treatment as described above, the prostate cancer eventually becomes resistant to the hormone treatment, and thus progresses to metastatic hormone-refractory (castration resistant) prostate cancer, and since the prognosis is poor because the patient's survival period is only 9 to 13 months, active treatment is required. From this time on, docetaxel may be prescribed as chemotherapy, but there is a problem in that the side effects of chemotherapy are intolerable because most patients with prostate cancer are elderly.

Polo-like kinase 1 (PLK1), which is a member of the PLK family, is a kinase protein which is expressed only in proliferating adult tissues and dividing cells, and the expression level of PLK1 serves as an index of cell proliferation and can track various malignant cancers. In addition, it has been reported that high expression levels of PLK1 in cancer tissues are associated not only with proliferation but also with metastasis, P53 mutation, which is a typical cause involved in cancer malignancies in various cancer tissues, and it is known that mutations in P53 cause the activation of PLK1, which causes malignant cancer.

PLK1 is a serine/threonine phosphatase, and corresponds to a core signal of cancer cell proliferation by cell division that regulates centrosome formation, bipolar spindle formation, the chromosomal skeleton, and cleavage furrow formation, but PLK1 is activated in the process of cancer cell proliferation to activate cdc25c, and the activated cdc25c induces mitosis of cancer cells by dephosphorylating cyclin B1. The mitosis of cancer cells eventually leads to cancer cell proliferation, and accordingly, many synthetic PLK1 inhibitors have entered clinical trials such as Volasertib, which is an inhibitor of PLK1, recently approved as an orphan drug therapeutic agent for blood cancer. Furthermore, recently, PLK1 has not only attracted attention as a therapeutic target in various types of hematological and solid cancers, but its applicability as a drug target in an anticancer drug-resistant carcinoma such as gemcitabine-resistant pancreatic cancer cell and imatinib-resistant chronic myelogenous leukemia has also been suggested. However, there has been no evaluation of the therapeutic potential of PLK1 for castration-resistant prostate cancer to date.

DISCLOSURE

Technical Problem

The present invention has been devised to solve the problem in the related art as described above, and as a result of intensive studies to develop a drug that inhibits PLK1 activity, the present inventors first confirmed that 2,4,6-trihydroxyacetophenone (THA), which is a main ingredient of *Curcuma comosa*, inhibited the progression of prostate cancer by causing the inhibition of PLK1 activity, thereby completing the present invention.

Thus, an object of the present invention is to provide a pharmaceutical composition including 2,4,6-trihydroxyacetophenone (THA) represented by the following Chemical Formula 1 or a pharmaceutically acceptable salt thereof as an effective ingredient for prevention or treatment of prostate cancer.

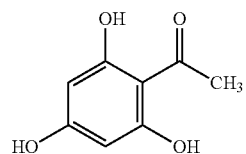

[Chemical Formula 1]

However, technical problems to be achieved by the present invention are not limited to the aforementioned problems, and other problems that are not mentioned may be clearly understood by those skilled in the art from the following description.

Technical Solution

To solve the object of the present invention as described above, the present invention provides a pharmaceutical composition including 2,4,6-trihydroxyacetophenone (THA) represented by the following Chemical Formula 1 or a pharmaceutically acceptable salt thereof as an effective ingredient for prevention or treatment of prostate cancer.

[Chemical Formula 1]

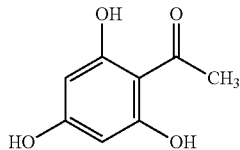

As an exemplary embodiment of the present invention, the THA may be extracted from *Curcuma comosa*.

As another exemplary embodiment of the present invention, the prostate cancer may be prostate cancer overexpressing polo-like kinase-1 (PLK1).

As still another exemplary embodiment of the present invention, the pharmaceutical composition may inhibit Polo-like kinase 1 (PLK1) activity.

As yet another exemplary embodiment of the present invention, the pharmaceutical composition may inhibit the activity of cdc25c or cyclin B1.

As yet another exemplary embodiment of the present invention, the pharmaceutical composition may be characterized by increasing caspase-3/7 activity.

As yet another exemplary embodiment of the present invention, the pharmaceutical composition may be characterized by increasing an apoptotic index.

Furthermore, the present invention provides a method for treating prostate cancer, the method including administering a pharmaceutical composition including 2,4,6-trihydroxyacetophenone (THA) as an effective ingredient to an individual in need of treatment for prostate cancer.

Moreover, the present invention provides a use of a pharmaceutical composition including 2,4,6-trihydroxyacetophenone (THA) as an effective ingredient for treatment of prostate cancer.

Advantageous Effects

The present invention relates to a composition including 2,4,6-trihydroxyacetophenone (THA) as an effective ingredient for prevention or treatment of prostate cancer, and the THA of the present invention is a main ingredient of *Curcuma comosa*. The composition of the present invention effectively inhibits the growth of prostate cancer by inhibiting, particularly, the activity of polo-like kinase 1 (PLK1) and thus is expected to find useful application in the prevention, alleviation, and treatment of prostate cancer in future.

MODES OF THE INVENTION

Figure 1:
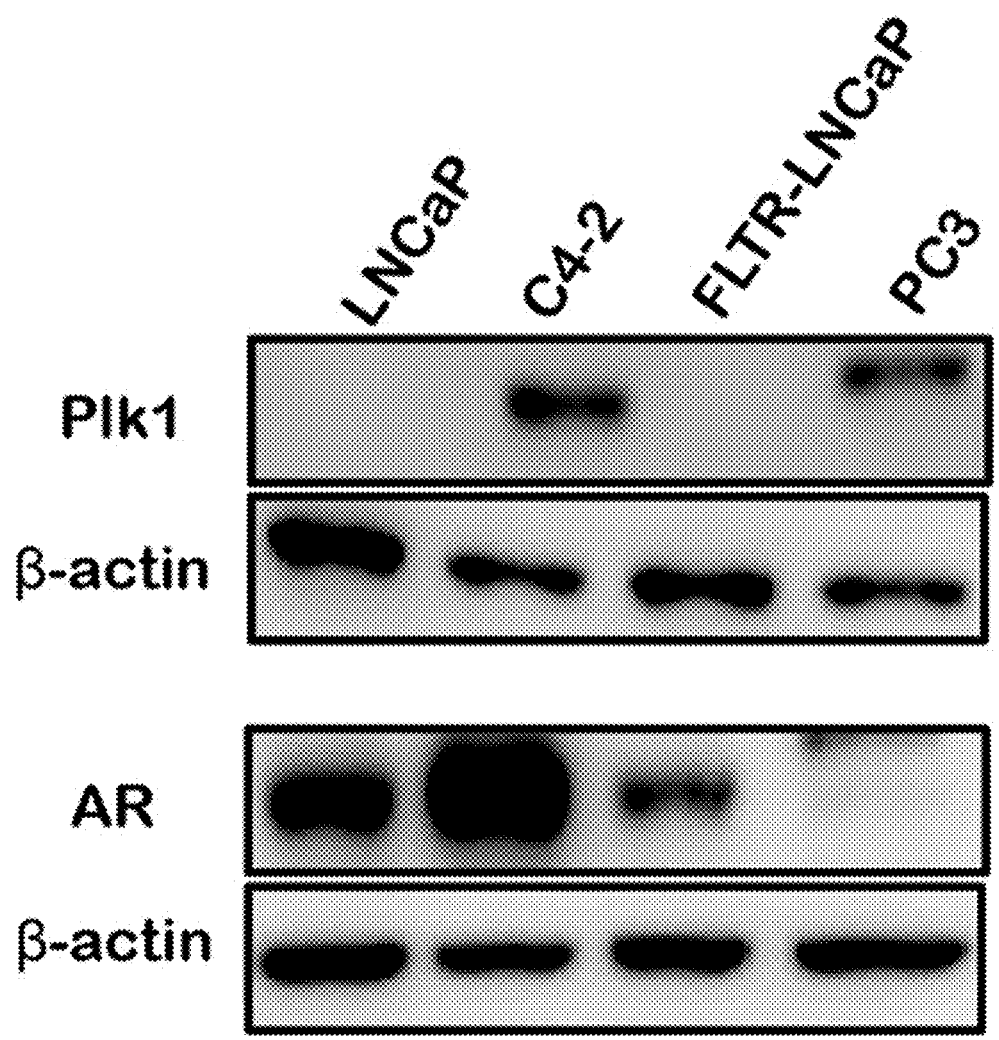
FIG. 1 is a view illustrating the results of confirming changes in expression of PLK1 and the androgen receptor in prostate cancer cell lines.

As a result of intensive studies on methods for treating prostate cancer, the present inventors confirmed that 2,4,6-trihydroxyacetophenone (THA), which is a main ingredient of *Curcuma comosa*, was effective in inhibiting the proliferation of prostate cancer particularly through PLK1 inhibitory activity, thereby completing the present invention based on this.

Hereinafter, the present invention will be described in detail.

In an exemplary embodiment of the present invention, changes in expression of PLK1, the androgen receptor and downstream proteins in prostate cancer cell lines were confirmed (see Example 2).

In another exemplary embodiment of the present invention, cell proliferation inhibitory effects of prostate cancer cells according to treatment with 2,4,6-trihydroxyacetophenone (THA) were confirmed (see Example 3), and effects of increasing apoptosis according to treatment with THA were also confirmed (see Example 4).

In still another exemplary embodiment of the present invention, the effects of blocking the cell cycle of prostate cancer cells according to treatment with THA were confirmed (see Example 5).

Accordingly, 2,4,6-trihydroxyacetophenone (THA) according to the present invention may be used for various purposes and uses in which prevention or treatment of prostate cancer is required.

Thus, the present invention provides a pharmaceutical composition including 2,4,6-trihydroxyacetophenone (THA) represented by the following Chemical Formula 1 or a pharmaceutically acceptable salt thereof as an effective ingredient for prevention or treatment of prostate cancer.

[Chemical Formula 1]

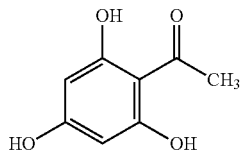

The term "prevention" used herein refers to all actions that inhibit or delay the onset of prostate cancer or castration-resistant prostate cancer by administration of the pharmaceutical composition of the present invention.

The term "treatment" used herein refers to all actions that ameliorate or beneficially change symptoms caused by prostate cancer or castration-resistant prostate cancer by administration of the pharmaceutical composition of the present invention.

The term "pharmaceutically acceptable" used herein refers to a compound or composition which is suitable for use in contact with tissues of a subject (for example: a human) and within the scope of the sound medical judgment because its benefit/risk ratio is reasonable without excessive toxicity, irritation, allergic reactions or other problems or complications.

As the term "salt" used herein, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylates, phenyl-substituted alkanoates, hydroxyalkanoates and alkanedioates, aromatic acids, aliphatic and aromatic sulfonic acids. Such pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphates chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, β-hydroxybutyrates, glycolates, malates, tartrates, methanesulfonates, propanesulfonates, naphthalene-1-sulfonates, naphthalene-2-sulfonates or mandelates.

The acid addition salt according to the present invention may be prepared by typical methods, for example, dissolving a compound represented by Chemical Formula 1 in an excess aqueous acid solution, and precipitating this salt using a water-miscible organic solvent, for example, methanol, ethanol, acetone or acetonitrile. Further, the acid addition salt may also be prepared by evaporating the solvent or excess acid from this mixture, and then drying the mixture or suction-filtering a precipitated salt.

In addition, a pharmaceutically acceptable metal salt may be prepared using a base. An alkali metal or alkaline earth metal salt is obtained by, for example, dissolving the compound in an excess alkali metal hydroxide or alkaline-earth metal hydroxide solution, filtering the insoluble compound salt, evaporating the filtrate, and drying the resulting product. In this case, preparing a sodium, potassium or calcium salt as the metal salt is pharmaceutically suitable. A silver salt corresponding to this is obtained by reacting the alkali metal or alkaline earth metal salt with a suitable silver salt (for example, silver nitrate).

The pharmaceutical composition of the present invention may include a pharmaceutically acceptable carrier in addition to an active ingredient. In this case, the pharmaceutically acceptable carrier is typically used during formulation, and includes lactose, dextrose, sucrose, sorbitol, mannitol, starch, gum acacia, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, but is not limited thereto. Furthermore, the pharmaceutically acceptable carrier may further comprise a lubricant, a wetting agent, a sweetening agent, a flavoring agent, an emulsifier a suspending agent, a preservative, and the like in addition to the above ingredients.

The pharmaceutical composition of the present invention may be orally administered or may be parenterally administered (for example, applied intravenously, subcutaneously, intraperitoneally, or locally), and the administration dose may vary depending on a patient's condition and body weight, severity of disease, drug form, and administration route and period according to the target method, but the administration dose may be properly selected by those skilled in the art.

The pharmaceutical composition of the present invention is administered in a pharmaceutically effective amount. In the present invention, "pharmaceutically effective amount" means an amount sufficient to treat diseases at a reasonable benefit/risk ratio applicable to medical treatment, and an effective dosage level may be determined according to factors including the type of a patient's disease, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present invention may vary depending on the age, gender, condition, and body weight of a patient, the absorption of the active ingredients in the body, inactivation rate and excretion rate, disease type, and the drugs used in combination, and in general, 0.001 to 150 mg, preferably 0.001 to 100 mg of the pharmaceutical composition of the present invention per 1 kg of a body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

Cancer, which is a disease to be prevented or treated by the composition of the present invention, is classified as a disease in which normal tissue cells proliferate indefinitely for some reason and continue to grow rapidly regardless of the living phenomenon of the organism or the surrounding tissue condition, and the cancer in the present invention may be prostate cancer, but is not limited thereto.

The compound of the present invention is effective for preventing, ameliorating, or treating cancer by inhibiting the proliferation of cancer cells through PLK1 inhibitory activity.

In the present invention, the THA may be extracted from *Curcuma comosa*, may be obtained by any method known in the art for obtaining an extract from nature, and may be preferably obtained by a method for solubilizing and extracting an extract by adding water or an organic solvent.

The process of extracting the THA by adding water or an organic solvent to *Curcuma comosa* may be performed while a resulting solution is stirred or allowed to stand, the THA may be extracted by performing a hot water extraction method, a cold water extraction method, a reflux cooling extraction method, an ultrasonic extraction method, or the like once or several repeated times, and in this case, as the organic solvent which may be added, it is possible to use methanol, ethanol, propanol, isopropanol, butanol, acetone, ether, benzene, chloroform, ethyl acetate, methylene chloride, or the like, but the organic solvent is not limited thereto.

Furthermore, the present invention provides a method for treating prostate cancer, the method including administering the pharmaceutical composition to an individual. As used herein, the "individual" refers to a subject in need of treatment of a disease, and more specifically, refers to a mammal such as a human or a non-human primate, a rat, a mouse, a dog, a cat, a horse, and a cow.

Hereinafter, preferred examples for helping the understanding of the present invention will be suggested. However, the following examples are provided only to more easily understand the present invention, and the contents of the present invention are not limited by the following examples.

EXAMPLES

Example 1. Experimental Preparation and Experimental Method 1-1. Reagents and Materials Cleaved caspase-3 (CC3), Cdc25c, and Polo-like kinase 1 (PLK1) antibodies were purchased from Cell Signaling Technology (Beverly, Mass., USA), and Cyclin B1 (G2/mitotic-specific cyclin-B1) and androgen receptor (AR) antibodies and 2,4,6-trihydroxyacetophenone (THA) were purchased from Santa Cruz Biotechnology (Dallas, Tex. USA). Further, a phospho-HH3 (histone H3, PHH3) antibody was purchased from Biolegend (San Diego, Calif., USA).

INCUCYTE™ caspase-3/7 green apoptosis assay reagent was purchased from Essen Bioscience (Ann Arbor, Mich., USA), a β-actin antibody and flutamide were purchased from Sigma (St. Louis, Mo., USA), and *Curcuma comosa* was provided by KOREA UNITED PHARM INC and used.

1-2. Culture of Prostate Cancer Cell Line

LnCaP cells, PC3 cells which are androgen receptor (AR)-negative cells, and C4-2 cells showing castration resistance were cultured using an RPMI-1640 medium (Hyclone, Logan, Utah, USA) containing 10% fetal bovine serum (FBS) (Hyclone, Logan, Utah, USA) and 1% penicillin/streptomycin.

Flutamide-resistant LnCaP cells (FLTR-LNCaP cells) were constructed by culturing LnCaP cells in a medium containing 9% fetal bovine serum (Hyclone, Logan, Utah, USA) and 1% Charcoal-dextran fetal bovine serum (Gemini, West Sacramento, Calif., USA), and then treating the LnCaP cells with flutamide, and the concentration of the flutamide was gradually increased for about 12 months starting from 1 μM, and as a result, flutamide-resistant LnCaP cells which had acquired resistance at 30 μM were constructed.

1-3. Immunochemical Analysis

Sodium dodecyl sulfate-polyacrylamide gel electrophoresis (SDS-PAGE) was performed using a gel electrophoresis apparatus (Mighty Small SE250, Hoefer Scientific Instruments, San Francisco). After a cell lysate fraction was diluted in a sample dilution buffer solution [63 mM Tris (pH 6.8), 10% glycerol, 2% SDS, 0.0013% bromophenol blue, and 5% β-mercaptoethanol], electrophoresis was performed in an electrode buffer solution (15 g of Tris, 72 g of glycerin, and 5 g of SDS were contained in a 1 L solution) using 8 to 12% gel. Proteins were electrophoretically transferred from the gel to a nitrocellulose membrane at 190 mAmps for 70 minutes in a transfer buffer solution (25 mM Tris, 192 mM glycerin, and 20% v/v methanol (pH 8.3)) using a transfer electrophoresis apparatus. After a primary antibody was reacted with the nitrocellulose membrane, a secondary antibody was reacted with horseradish peroxidase-conjugated goat anti-rabbit IgG and horseradish peroxidase-conjugated goat anti-mouse IgG for 6 hours, and color was developed using an ECL chemiluminescence system (Amersham, Gaithersberg, Mass.).

1-4. Real-Time Cell Proliferation Analysis

In order to measure cell proliferation, cells were plated onto a 96-well dish ($5 \times 10^3$ cells/well). After treatment with a drug, the number of live cells was measured at 4-hour intervals using an INCUCYTE™ ZOOM Live Cell Analysis System (Essen Bioscience, Ann Arbor, Mich., USA).

1-5. Real-Time Apoptosis Analysis

In order to measure apoptosis, cells were plated onto a 96-well dish ($5 \times 10^3$ cells/well). The INCUCYTE™ ZOOM 96-well Caspase-3/7 apoptosis assay reagent (Essen Bioscience, Ann Arbor, Mich., USA) was pretreated for 3 hours, a drug was treated, and then the fluorescence expression level was measured at 4-hour intervals using an INCUCYTE™ ZOOM Live Cell Analysis System (Essen Bioscience, Ann Arbor, Mich., USA).

1-6. Cell Cycle Analysis

In order to measure the cell cycle distribution, cells were plated onto a 100 mm dish ($5 \times 10^5$ cells/well). The cells were fixed with 4° C. PBS, refrigerated in 70% EtOH at 4° C., and cultured for 24 hours. After the 70% EtOH was removed, the PHH3 antibody was treated with a lysing solution composed of 1% bovine serum albumin/0.5% Triton X-100/0.2 mg/ml EDTA to a final concentration of 1:50, and then stained at 37° C. for 15 minutes. Thereafter, the lysing solution was removed, and staining was performed again at 37° C. for 15 minutes using propidium iodide (PI)/Triton X-100/DNAse-free RNAse A. Next, 20,000 cells per experimental group were analyzed using the FACSCALIBUR™ (flow cytometer from BD Biosciences, CA, USA) machine.

Example 2. Confirmation of PLK1 Expression Pattern in Prostate Cancer Cells 2-1. Confirmation of Changes in Expression of PLK1 and Androgen Receptor in Prostate Cancer Cells LnCaP, C4-2, PC3, and FLTR-LnCaP cells cultured by the method in Example 1-2 were plated onto a 6-well plate. After 36 hours had passed, changes in expression of polo-like kinase 1 (PLK1) and the androgen receptor (AR) were observed by the immunochemical analysis method in Example 1-3.

As a result, as illustrated in FIG. 1, the expression level of PLK1 was found to be high in C4-2 cells showing castration resistance and PC3 cells (AR-negative cells), and the expression level of AR was confirmed to be highest in C4-2 cells. Meanwhile, although FLTR-LNCaP cells were subjected to long-term treatment with an AR antagonist to cause flutamide resistance, the expression of PLK1 was not high. From the foregoing, it can be seen that PLK1 was selectively overexpressed in castration-resistant prostate cancer cells and AR-negative prostate cancer cells (PC3).

2-2. Confirmation of Changes in Expression of PLK1 and Downstream Proteins in Prostate Cancer Cells Among the prostate cancer cells cultured by the method in Example 1-2, 3 types, LNCaP, PC3, and C4-2 cells, were plated onto a 6-well plate, and 12 hours later, changes in expression of polo-like kinase 1 (PLK1) and cdc25c and cyclin B1 which are PLK1 subfactors were observed by the immunochemical analysis method in Example 1-3.

Figure 2A:
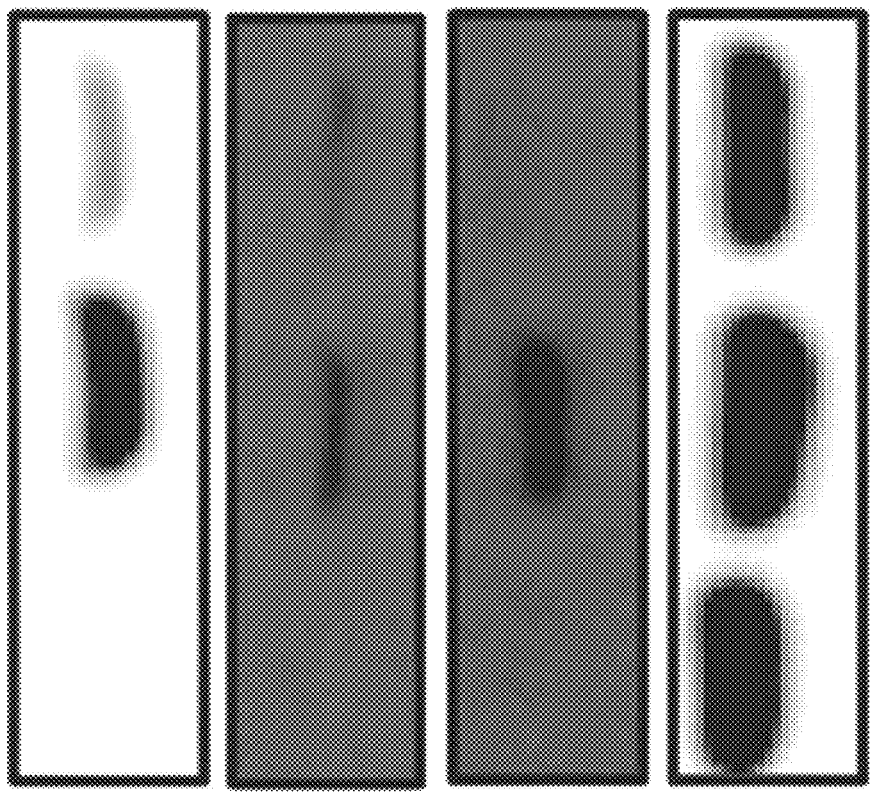
FIGS. 2A and 2B are views illustrating the results of confirming changes in expression of PLK1 and downstream proteins in prostate cancer cell lines.
Figure 2B:
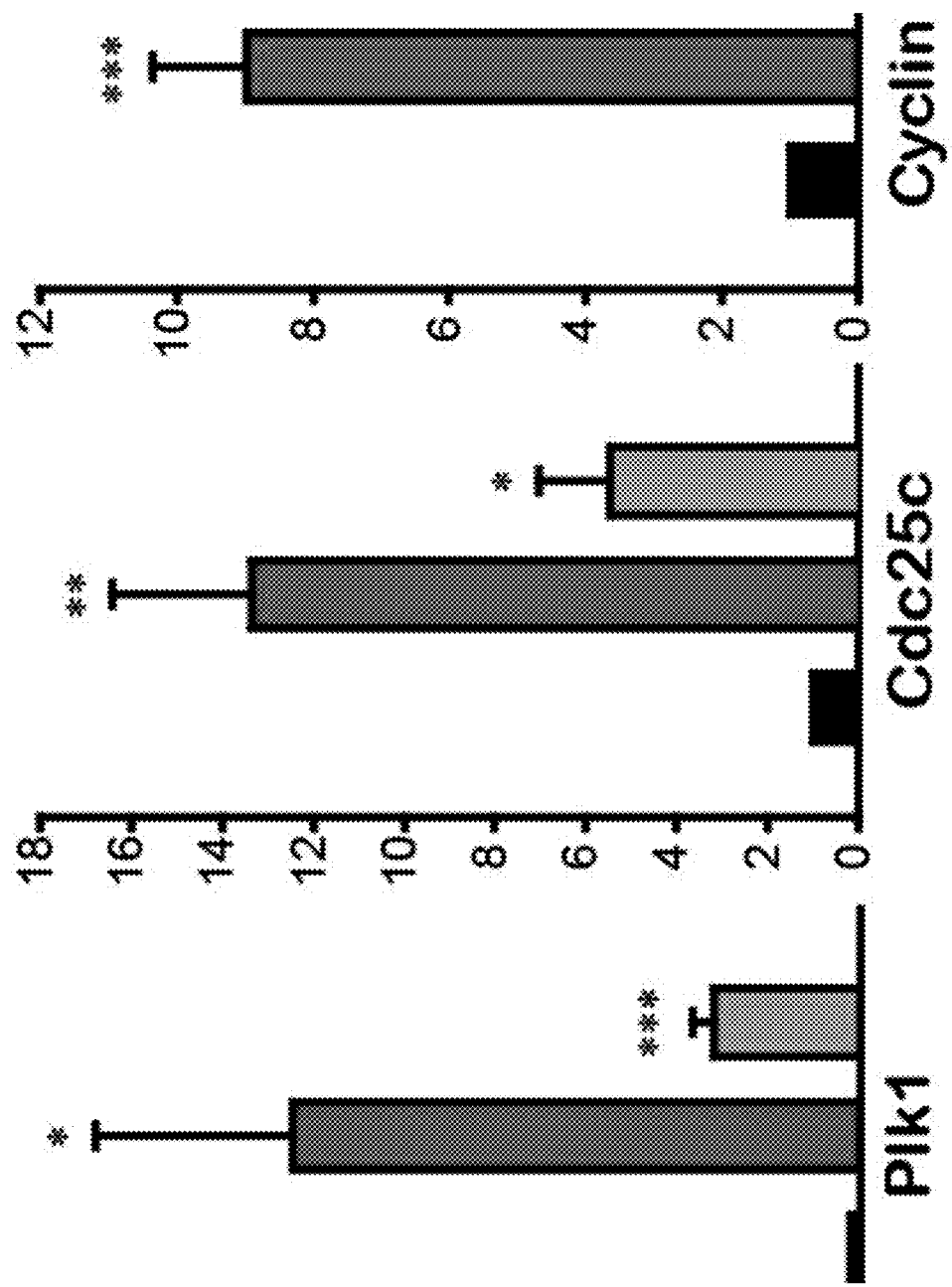

As a result, as illustrated in FIGS. 2A and 2B, it was confirmed that the expression levels of both cdc25c (M-phase inducer phosphatase 3) and cyclin B1 (G2/mitotic-specific cyclin-B1) in PC3 and C4-2 cells were increased, whereas there was no change in expression level in LNCaP cells. From the foregoing, it can be seen that activation of PLK1 subsignals is observed in cells with high PLK1 expression.

Example 3. Confirmation of Effect of Inhibiting Cell Proliferation of Prostate Cancer Cells According to Treatment with THA In order to comparatively observe the cell proliferation inhibitory effects after treatment of prostate cancer cells with THA, a 1 M solution was prepared by diluting 0.168 g of THA (molecular weight: 168.15) with 1 ml DMSO. After the prostate cancer cell lines (LnCaP, PC3, and C4-2) cultured by the method in Example 1-2 were treated with THA (3, 10, and 30 µM), PLK1 inhibitor BI2536 (1, 5, 10, 50, and 100 nM), and purpurogallin (PPG) (3, 10, 30, and 100 µM), the cell proliferation inhibitory effects were comparatively observed by the real-time cell proliferation analysis method for 68 hours according to Example 1-4 during.

Figure 3:
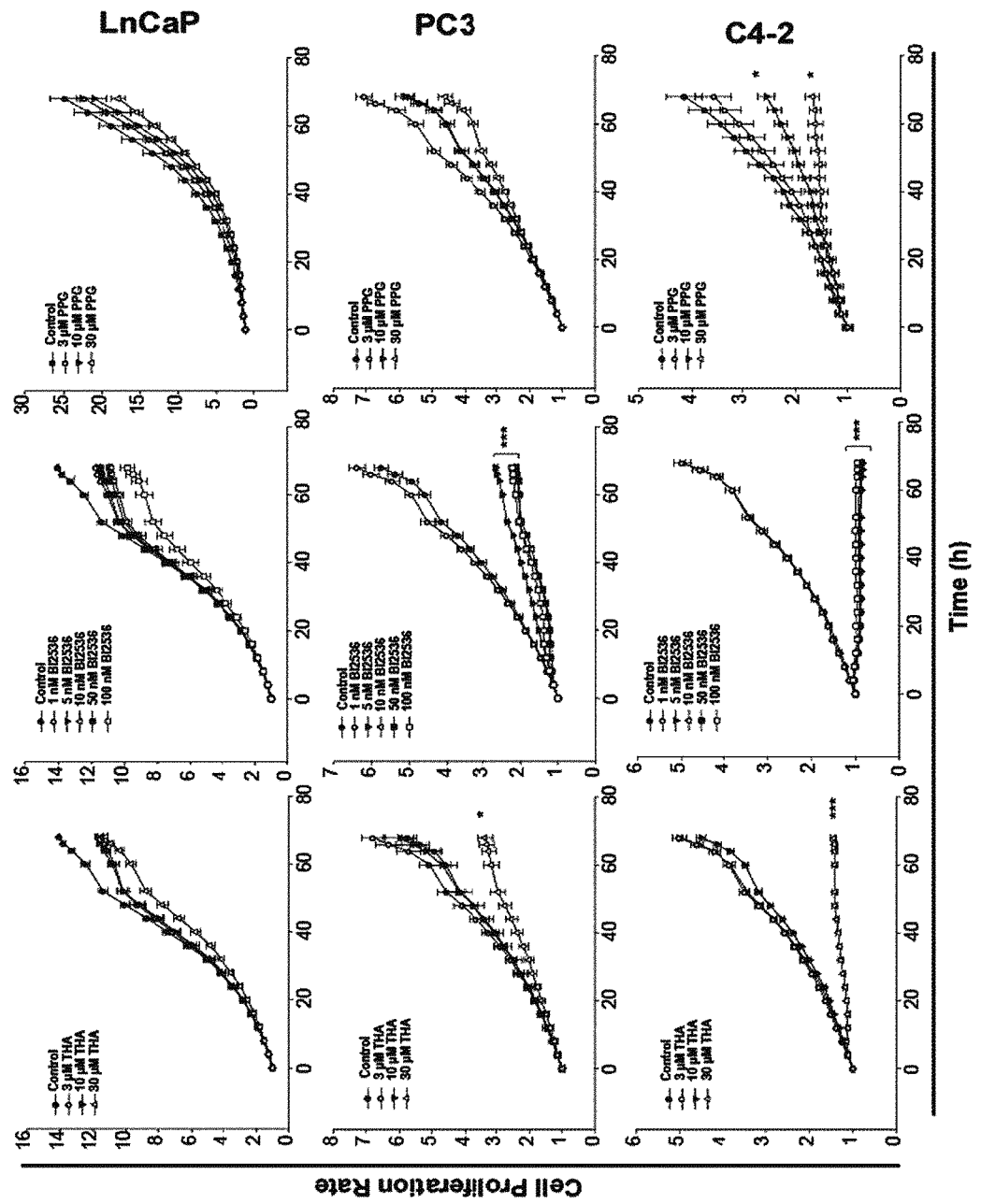
FIG. 3 is a set of graphs illustrating a comparison of cell growth inhibitory effects after treating prostate cancer cell lines with THA, BI2536, and purpurogallin (PPG).

As a result, as illustrated in FIG. 3, as a result of comparing the cell proliferation inhibitory effects among THA, BI2536, and purpurogallin in prostate cancer cells, THA exhibited the same cell proliferation inhibitory effects as BI2536 in PC3 and C4-2 cells.

From the foregoing, it can be seen that THA selectively inhibits cell proliferation in hormone-resistant prostate cancer cells (C4-2 and PC3) in which the expression of PLK1 was high, like BI2536, and it can be seen that in hormone-responsive LNCaP cells, 5-0% or more cell proliferation inhibition is not observed. Purpurogallin, which is known as a PLK1 polo-box domain inhibitor, showed limited cell proliferation inhibitory activity in LNCaP cells and PC3, and in C4-2 cells, a cell growth inhibitory effect that appeared to be non-selective only at a concentration of 100 uM was observed.

Example 4. Confirmation of Effect of Increasing Apoptosis of Prostate Cancer Cells According to Treatment with THA Caspase-3/7 is an enzyme that is selectively activated during the induction of mitochondrial-mediated or apoptotic receptor-mediated apoptosis, and in order to comparatively observe the effect of increasing apoptosis after prostate cancer cells were treated with THA, PC3 and C4-2 cells which are prostate cancer cell lines cultured by the method in Example 1-2 were treated with 30 µM THA and 5 nM BI2536, respectively, and then the degree of apoptosis was observed for 48 hours by quantifying a caspase-3/7 selective fluorescence substrate at 4-hour intervals using the INCUCYTE™ ZOOM Live Cell Analysis System (Essen Bioscience, Ann Arbor, Mich., USA).

Figure 4A:
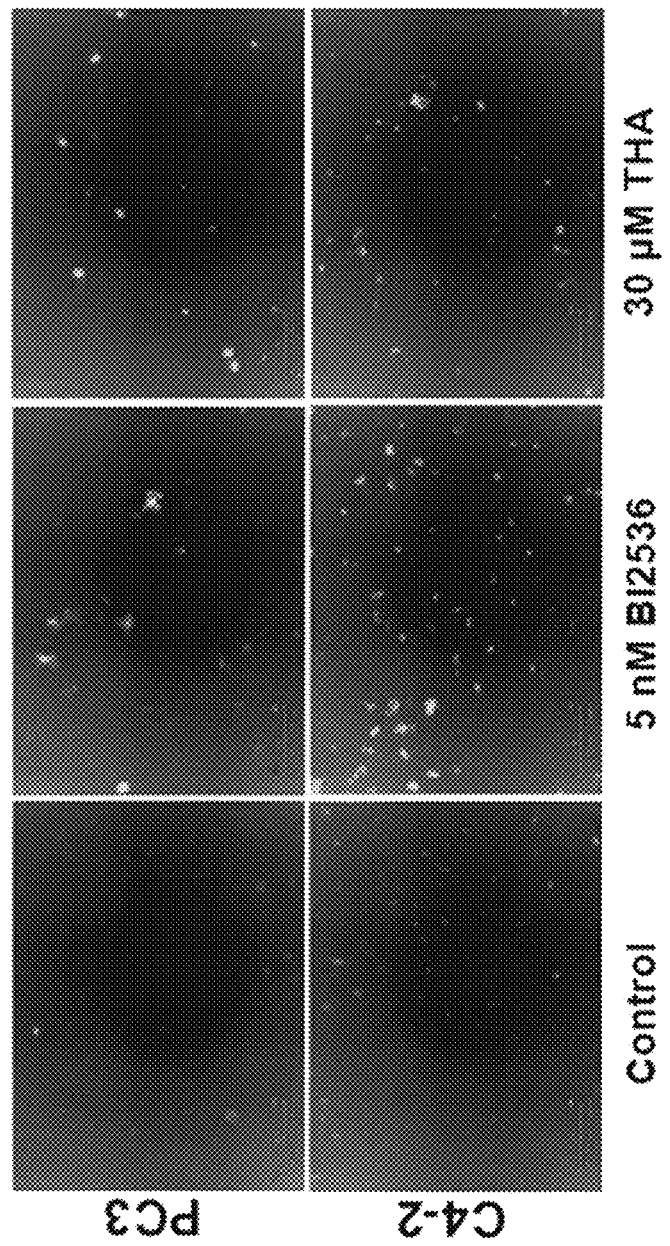
FIGS. 4A and 4B are views illustrating the results of confirming the degree of apoptosis through caspase-3/7 activity.
Figure 4B:
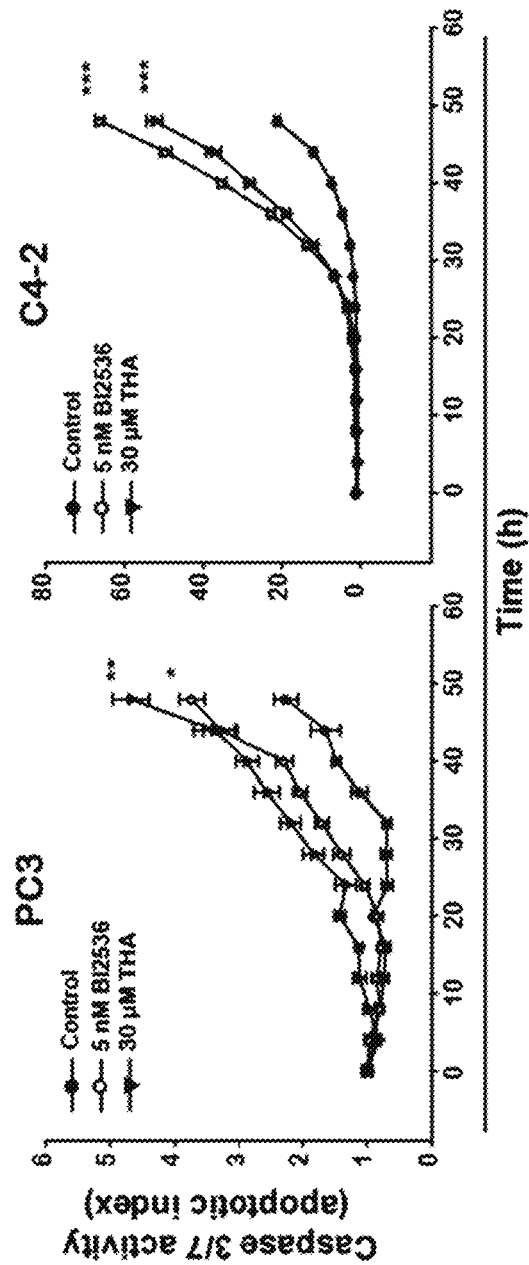

As a result, as illustrated in FIGS. 4A and 4B, it was confirmed that THA significantly increased the apoptotic index.

Further, the degree of apoptosis was observed by confirming the changes in expression of cleaved caspase-3 (CC3) which is an active-type caspase-3 during apoptosis, and first, the C4-2 and PC3 cells cultured by the method in Example 1-2 were plated onto a 6-well plate, and then cultured during 12 hr. And then the cells were treated with 30 µM THA or 5 nM BI2536 for 48 hours. Thereafter, the changes in expression of cleaved caspase-3 (CC3) were observed by the immunochemical analysis method in Example 1-3.

Figure 5A:
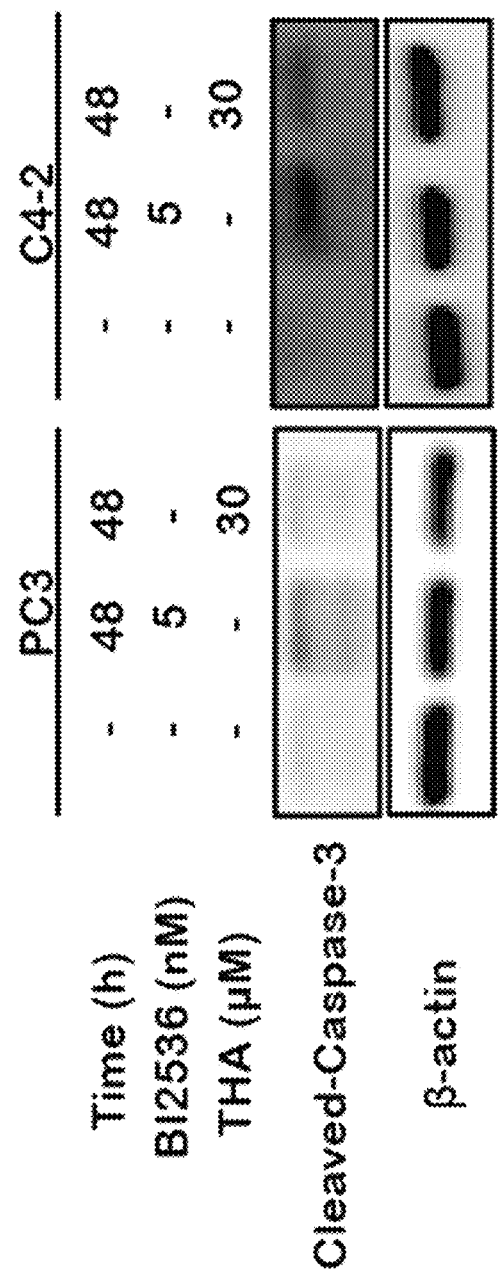
FIGS. 5A and 5B are views illustrating the results of confirming the degree of apoptosis through cleaved caspase-3 (CC3) expression levels.
Figure 5B:
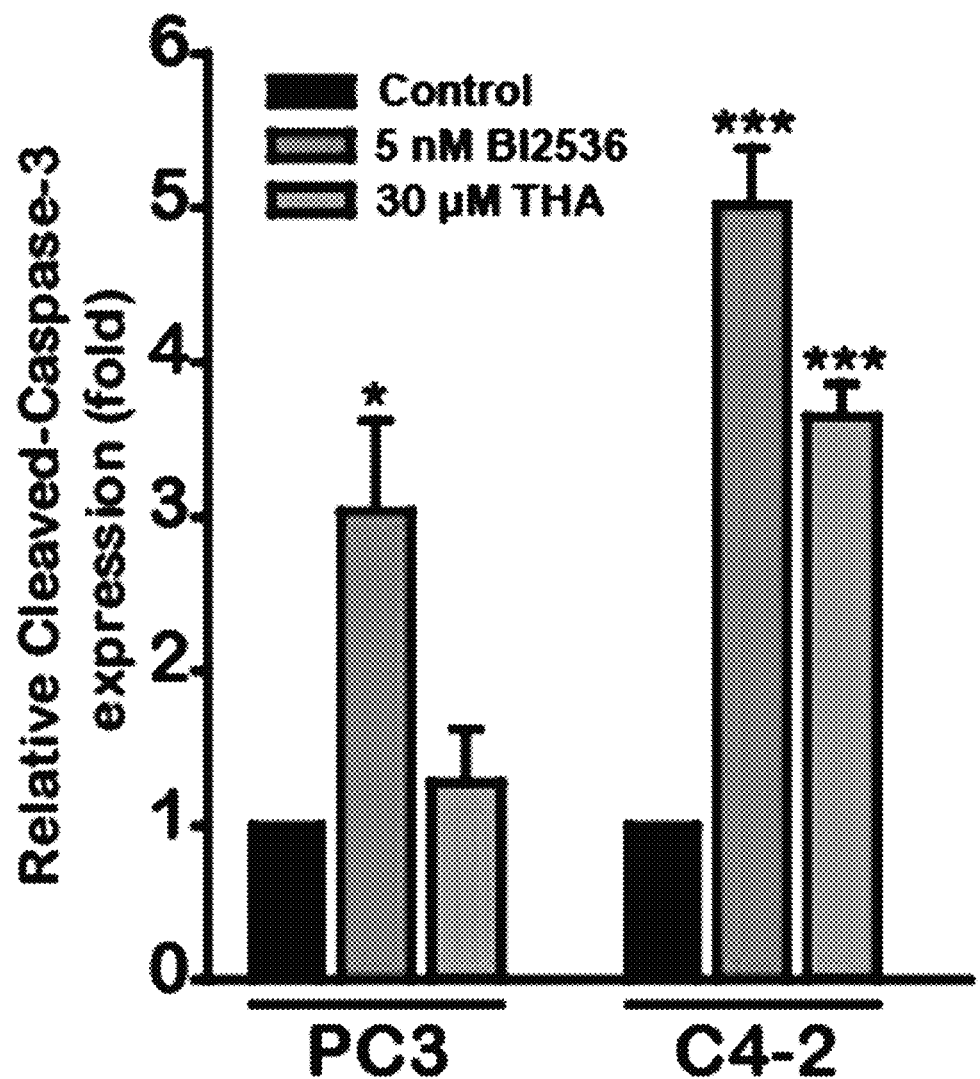

As a result, as illustrated in FIGS. 5A and 5B, it could be observed that the expression level of cleaved caspase-3 was increased, confirming that THA significantly increased the apoptotic index. From the foregoing, it can be seen that in PC3 and C4-2 cells, which are hormone-resistant prostate cancer cells, apoptosis is effectively induced during treatment with either THA or BI2536.

Example 5. Confirmation of Effect of Blocking Cell Cycle of Prostate Cancer Cells According to Treatment with THA PLK1 is a representative G2/M cell cycle regulatory phosphatase, and in order to confirm the effect of blocking the cell cycle of prostate cancer cells according to the treatment with THA, the PC3 cells cultured by the method in Example 1-2 were plated onto a 6-well plate, and then 12 hours later, the cells were treated with 30 µM THA and 5 nM BI2536 for 24 hours. Thereafter, changes in the cell distribution of each of the sub-G1, S, and G2/M phases and the proportion of PH3-positive cells (M phase marker) were observed by the method in Example 1-6.

Figure 6A:
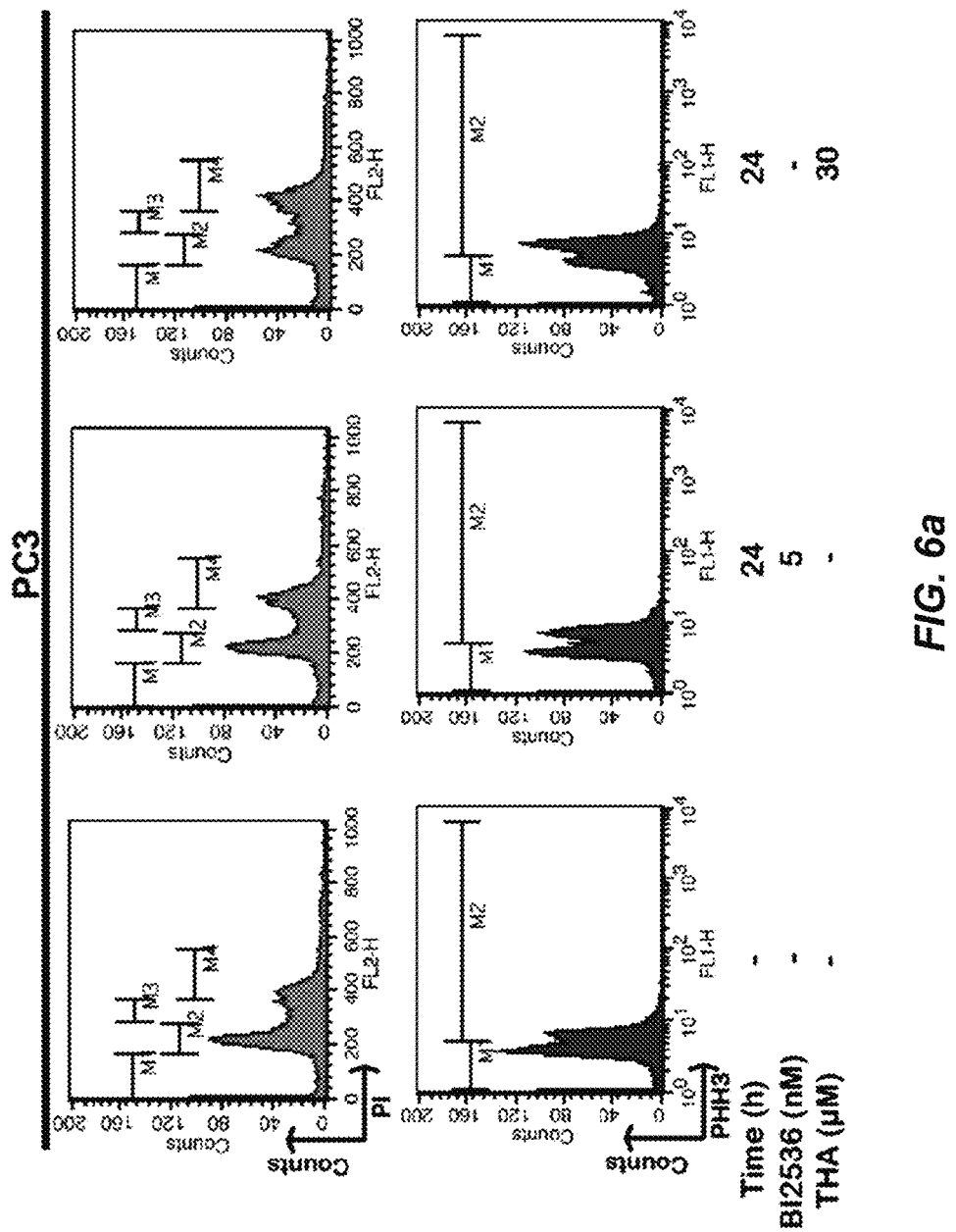
FIGS. 6A and 6B are views illustrating the results of confirming the cell cycle blocking effects after treating prostate cancer cell lines with THA and BI2536.
Figure 6B:
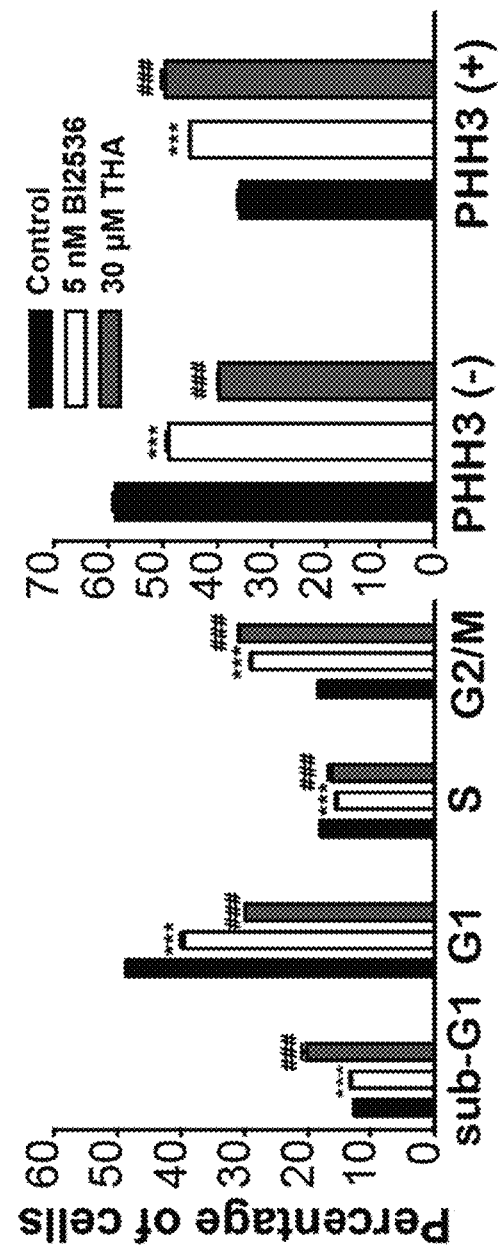

As a result, as illustrated in FIGS. 6A and 6B, it could be confirmed that THA selectively blocked cell cycle progression at the G2/M phase, 30% or more cells were observed in the G2/M phase during the treatment with cycleBI2536 or THA, and even during the quantification of PHH3-positive cells, a significant increase was observed compared to the control. Therefore, from the foregoing, it can be seen that the inhibition of G2/M phase progression is induced upon treatment with THA and BI2536 in PC3 cells, which are hormone-resistant prostate cancer cells.

From the foregoing, it can be seen that THA selectively acts on prostate cancer cells with high PLK1 expression, and thus it is expected that THA can be effectively utilized in the treatment of PLK1-positive prostate cancer in the future.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

The THA of the present invention is a main ingredient of *Curcuma comosa*, and the composition of the present invention effectively inhibits the proliferation of prostate cancer by particularly inhibiting the activity of polo-like kinase 1 (PLK1), and thus is expected to be usefully used in related industrial fields such as the medical industry because the composition of the present invention can be used for the prevention, alleviation, and treatment of prostate cancer.

The invention claimed is:

1. A method for treating prostate cancer, the method comprising administering a pharmaceutical composition comprising 2,4,6-trihydroxyacetophenone (THA) represented by the following Chemical Formula 1 or a pharmaceutically acceptable salt thereof as an effective ingredient to a subject in need of treatment for prostate cancer, wherein the prostate cancer is prostate cancer with overexpressed polo-like kinase-1 (PLK1):

[Chemical Formula 1]

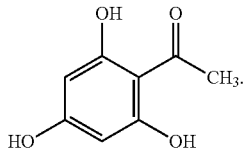

* * * * *